US008062843B2

(12) United States Patent
Donner et al.

(10) Patent No.: US 8,062,843 B2
(45) Date of Patent: Nov. 22, 2011

(54) USE OF ACETALS FOR ISOLATION OF NUCLEIC ACIDS

(75) Inventors: Horst Donner, Penzberg (DE); Frank Bergmann, Iffeldorf (DE); Nina Lassonczyk, Penzberg (DE); Bernd Buchberger, Zeitlarn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 178 days.

(21) Appl. No.: 12/480,981

(22) Filed: Jun. 9, 2009

(65) Prior Publication Data

US 2010/0086923 A1    Apr. 8, 2010

(30) Foreign Application Priority Data

Dec. 13, 2006  (EP) .................................... 06025778

(51) Int. Cl.
*C12Q 1/68*    (2006.01)
*C07H 21/00*    (2006.01)
(52) U.S. Cl. .......................................... 435/6; 536/25.4
(58) Field of Classification Search ........ 435/6; 536/25.4
See application file for complete search history.

(56) References Cited

U.S. PATENT DOCUMENTS

| | | | | |
|---|---|---|---|---|
| 5,004,543 | A * | 4/1991 | Pluskal et al. ................ | 210/490 |
| 5,234,809 | A | 8/1993 | Boom et al. | |
| 5,961,801 | A | 10/1999 | Hui-Shieh et al. | |
| 6,383,393 | B1 | 5/2002 | Colpan et al. | |
| 6,905,825 | B2 | 6/2005 | Kojima et al. | |
| 2001/0009960 | A1* | 7/2001 | Sato et al. ....................... | 536/63 |
| 2001/0025005 | A1* | 9/2001 | Williams ....................... | 502/102 |
| 2002/0086326 | A1* | 7/2002 | Smith et al. ........................ | 435/6 |
| 2002/0128364 | A1* | 9/2002 | Michot et al. .................. | 524/401 |
| 2002/0164572 | A1* | 11/2002 | Lin et al. .............. | 435/2 |
| 2002/0192667 | A1 | 12/2002 | Kojima et al. | |
| 2004/0019196 | A1* | 1/2004 | Bair et al. .................... | 536/25.4 |
| 2004/0138090 | A1* | 7/2004 | Drapier et al. ................. | 510/506 |
| 2004/0180445 | A1* | 9/2004 | Domanico et al. .............. | 436/17 |
| 2004/0267024 | A1* | 12/2004 | Wang et al. .................... | 548/252 |
| 2005/0079535 | A1 | 4/2005 | Kirchgesser et al. | |
| 2005/0123965 | A1* | 6/2005 | Yamashita et al. ............... | 435/6 |
| 2006/0029972 | A1* | 2/2006 | Lorenz ................ | 435/6 |
| 2008/0146789 | A1* | 6/2008 | Braman et al. ............... | 536/25.3 |
| 2008/0280997 | A1* | 11/2008 | Rodier et al. ................ | 514/772 |

FOREIGN PATENT DOCUMENTS

| | | |
|---|---|---|
| DE | 3724442 A1 | 2/1989 |
| EP | 0768773 A1 | 10/1996 |
| EP | 1529814 A1 | 5/2005 |
| WO | 9916781 A2 | 4/1999 |
| WO | 0137291 A1 | 5/2001 |

OTHER PUBLICATIONS

Perkin Elmer Cetus GeneAmp DNA Amplification Reagent Kit Product instructions (1988).*
http://en.wikipedia.org/wiki/1,3-Dioxane.*
http://en.wikipedia.org/wiki/1,4-Dioxane.*
Penczek et al. Progress in polymerization of cyclic acetals. In Ring-opening polymerization : Saegusa et al. ACS Symposium Series : Am. Chemical Society, Washington, DC,1977.*
http://en.wikipedia.org/wiki/Ether  http://en.wikipedia.org/wiki/Acetal.*
Bartl, K. et al., "Simple and Broadly Applicable Sample Preparation by Use of Magnetic Glass Particles," Clin Chem Lab Med 36:8 (1998) 557-559.
Boom, R. et al., "Rapid and Simple Method for Purification of Nucleic Acids," Journal of Clinical Microbiology 28:3 (Mar. 1990) 495-503.
Cox, A., "The Use of Guanidinium Chloride in the Isolation of Nucleic Acids," Methods Enzymol 12B (1968) 120-129.
Greene, T. et al., Protective Groups in Organic Synthesis , John Wiley and Sons, Inc., New York (1999) 308-322, 724-727.
Jakobi, R. et al., "Filter-Supporter Preparation of Λ Phage DNA," Analytical Biochemistry 175 (1988) 196-201.
Mullis, K. et al., "Specific Synthesis of DNA in Vitro via a Polymerase-Catalyzed Chain Reaction," Methods in Enzymology 15 (1987) 335-350.
Sambrook et al., Molecular Cloning, A Laboratory Manual, 3rd Edition, CSHL Press 2001.
Schmitt, M. et al., "A rapid and simple method for the preparation of RNA from *Saccaromyces cerevisiae*," Nucleic Acids Research 18:10 (1990) 3091-3092.
Stallcup, M. et al., "Region-specific Initiation of Mouse Mammary Tumor Virus RNA Synthesis by Endogenous RNA Polymerase II in Preparation of Cell Nuclei, The Journal of Biological Chemistry," 258:10 (1983) 2802-2807.
Vogelstein, B. et al., "Preparative and analytical purification of DNA from agarose," Proc. Natl. Acad. Sci. USA 76:2 (Feb. 1979) 615-619.
Watson, J. et al., "Molecular Structure of Nucleic Acids," Nature 171:4356 (1953) 737-738.

* cited by examiner

*Primary Examiner* — Ethan C Whisenant

(57) ABSTRACT

The invention provides the use of water-miscible liquid cyclic acetals for adsorbing a nucleic acid to a solid phase such as a substrate with a silica surface. To this end, the invention also provides compositions comprising said acetals. Methods are disclosed and claimed to purify nucleic acids from samples, as well as kits useful for performing these methods. The nucleic acids purified by a method of the invention are suited for assays aiming at the detection of a target nucleic acid.

17 Claims, No Drawings

USE OF ACETALS FOR ISOLATION OF NUCLEIC ACIDS

RELATED APPLICATIONS

This application is a continuation of PCT/EP2007/010795 filed Dec. 11, 2007 and claims priority to EP 06025778.9 filed Dec. 13, 2006.

FIELD OF THE INVENTION

The present invention is directed to the purification of a nucleic acid. Particularly, the invention is directed to methods of adsorbing a nucleic acid present in an aqueous adsorption solution to a solid phase.

BACKGROUND OF THE INVENTION

Since the structure of DNA was deciphered by Watson & Crick in 1953 (Watson, J. D. and Crick, F. H. C., Nature 171 (1953) 737-738) investigation and handling of nucleic acids becomes an integral part of biochemistry molecular biology. Despite the availability of a number of isolation methods an commercial kits for performing such methods, new developments for fast and easy isolation or purification of nucleic acids with high yield and purity are still of major importance.

Nucleic acids are highly susceptible to enzymatic degradation. In 1968 Cox described the chaotropic agent guanidine HCl as an inhibitor of enzymatic nuclease activity (Cox, R. A., Methods Enzymol 12B (1968) 120-129). Besides a strong denaturing effect on proteins high concentrations of chaotropic agents also mediate cell lysis. Therefore chaotropic agents, particularly guanidine thiocyanate, are widely in use for nucleic acid isolation.

A first principle of nucleic acid isolation from a biological sample uses an organic solvent, particularly phenol, for the separation of nucleic acids from the remaining organic sample components. The phenol extraction is followed by a salt precipitation of the nucleic acid from an aqueous phase (Stallcup, M. R. and Washington, L. D., J. Biol. Chem. 258 (1983) 2802-2807, and Schmitt, M. E., et al., Nucl. Acid Res. 18 (1990) 3091-3092). Although this method results in nucleic acids with high yield and purity the major drawbacks are the use of poisonous reagents, the time consuming and labor intensive workflow. Due to these disadvantages automation of this isolation principle is not amenable to automation, or only to a very limited extent.

Another principle of nucleic acid isolation makes use of solid inorganic material, particularly silica, to which nucleic acids are adsorbed from an aqueous liquid phase such as a lysate of a biological sample. In 1979 Vogelstein and Gillespie described a method for isolating nucleic acid from agarose gel slices by binding nucleic acids to silica particles in presence of highly concentrated sodium iodide (Vogelstein, B. and Gillespie, D., Proc. Natl. Acad. Sci. USA 76 (1979) 615-619).

In addition it was found that the binding of nucleic acids to the solid phase was increased by the addition of anionic or cationic or neutral detergents, in particular TRITON-X100 (Union Carbide Chemicals & Plastics Technology Corporation), sodium dodecyl sulfate, NP40, and TWEEN 20 (ICI Americas Inc.).

Adsorption of a nucleic acid to the solid phase is usually performed in the presence of a potent denaturant such as a chaotropic agent (Boom, R. et al., J. Clin. Microbiol. 28 (1990) 495-503; U.S. Pat. No. 5,234,809). For the isolation process the biological material is mixed with a solution containing the denaturant. The resulting mix is brought into contact with the solid phase material whereby nucleic acid molecules are bound to the surface of the solid phase. Afterwards the solid material is washed with solutions containing decreasing chaotropic salt concentrations and increasing alcohol concentrations, in particular ethanol, in order to further purify the bound nucleic acids from other organic material and contaminating agents. In the last step the solid material is brought into contact with a low salt solution or water under alkaline pH in order to remove the bound nucleic acid from the solid phase. The complete workflow comprises a sample lysis step, a binding step, one or more washing steps, and an elution (desorption) step.

The solid phase can be arranged in different conformations. In a first design the solid phase is in fleece shape and embedded in a plastic device. An example therefor is a micro spin column (EP 0 738 733). This design is preferentially used in workflows which are performed manually. In a second design magnetic silica particles are used as a solid phase (Bartl, K., et al., Clin. Chem. Lab. Med. 36 (1998) 557-559). This design is preferentially used in automated workflows.

A further improvement of this method was observed when aliphatic alcohol (i.e., ethanol or isopropanol) or polyethylene glycol is added to the solution at the binding step (U.S. Pat. No. 6,383,393).

US 2002/10192667 A1 discloses purification of nucleic acids by addition (in buffer) of a chaotrope and an organic solvent such as the cyclic ether compound 1,4-dioxane, after which the mixture is passed by an inorganic support such as silica, onto which the nucleic acids bind. Other examples of added organic solvents in the binding buffer include the aliphatic ethers ethylene glycol dimethyl ether, ethylene glycol diethyl ether, propylene glycol dimethyl ether, propylene glycol diethyl ether, diethylene glycol dimethyl ether, diethylene glycol diethyl ether, tetrahydrofuran, the aliphatic esters propylene glycol monomethyl ether acetate, and ethyl lactate, and the aliphatic ketones hydroxyacetone, acetone, and methyl ethyl ketone.

US 2005/0079535 discloses the use of acetone, acetylacetone, acetonitrile, dimethylsulfoxide, diethylketone, methylethylketone, methylpropylketone, isobutylmethylketone, gamma-butyrolactone, gamma-valerolactone, propylene carbonate, and N-methyl-2-pyrrolidone as well as the use of the cyclic diether dioxane in the binding buffer, in order to adsorb a nucleic acid to a solid phase such as silica.

The methods for the isolation/purification of nucleic acids of the state of the art have certain disadvantages. Such disadvantages relate to, e.g., purity, selectivity, recovery rate, laboratory safety and convenience, as well as to the speed of the isolation/purification process.

E.g., in protocols using a phenol/chloroform extraction, residual phenol is often a problem for certain post isolation procedures, particularly for enzymatic reactions such as a digestion with a restriction enzyme, the polymerase chain reaction (PCR), or a ligase-mediated reaction. Generally, elevated concentrations of residual reagents from the purification/isolation process may pose a problem. It is therefore desired to keep residual amounts of the reagents used during the purification procedure as low as possible in the purified nucleic acid. Another potential problem related to purity is the coextraction of certain substances from the adsorption matrix (leaching). It is therefore desired to keep residual amounts of compounds liberated during the purification procedure by leaching as low as possible in the purified nucleic acid.

The chemical properties of the reagents used in the isolation/purification process determines the quality of the nucleic (yield, purity and size) as well as their performance in downstream workflows, including polymerase or reverse transcriptase based enzymatic reactions (Mullis, K. and Faloona, F. A., Methods Enzymol 155 (1987) 335-350). Furthermore, additional properties of the reagents like toxicity, as well as physical and chemical aspects like flash point and vapor pressure are of major importance.

Hazardous substances often bear environmental risks and cause high costs for waste management. Their use can be restricted based on the required technical and/or operational safety measures to be taken. The hazardous potential of buffers used in the isolation/purification of nucleic acids is chiefly influenced by the choice of the organic compound which promotes adsorption of the nucleic acid to the solid phase. With respect to the environmental burden it is desired to reduce the use of toxic or harmful agents as far as possible. Also, the flash point of a flammable organic compound, that is the lowest temperature at which it can form an ignitable mixture with oxygen, is desired to be high. This parameter particularly influences the costs of production of kits for nucleic acid purification. An organic compound with a flash point below room temperature has to be handled in specially equipped production facilities which prevent the development of explosive vapour. In addition, restrictions apply to the transport of such organic compounds. A low flash point is usually correlated with a high vapor pressure. As a consequence, certain organic compounds, particularly lower alcohols, tend to evaporate from solutions and therefore lead to variations in concentration over time. This effect also influences stability during storage as well as the handling of liquids with a high vapor pressure in an automated pipetting instrument. Avoiding substances with low flash points and a tendency to evaporate in the isolation/purification process would make the production of solutions for the purification of nucleic acids simpler and more economical. In addition, compounds with a low vapour pressure are desired as they increase the utility of nucleic acid isolation kits by eliminating a major source of pipetting error, thereby increasing the reliability of such kits.

The problem underlying the present invention therefore was to provide alternative compounds to promote the adsorption of a nucleic acid to a solid phase.

The inventors have surprisingly found that adsorption of a nucleic acid to a solid phase is effectively accomplished when a water-miscible liquid cyclic acetal is used in the adsorption solution.

SUMMARY OF THE INVENTION

Therefore, a first aspect of the invention is a composition comprising a water-miscible liquid cyclic acetal, an aqueous buffer, and a chaotropic agent. Another aspect of the invention is the use of a water-miscible liquid cyclic acetal for adsorbing a nucleic acid onto a solid phase. A further aspect of the invention is a method of using a water-miscible liquid cyclic acetal and a nucleic acid in a sample comprising the steps of (a) providing the nucleic acid in a sample, whereby the sample is dissolved in a liquid composition comprising a water-miscible liquid cyclic acetal, an aqueous buffer, and a chaotropic agent; followed by (b) providing the solid phase and contacting the liquid composition of step (a) with the solid phase, thereby adsorbing the nucleic acid onto the solid phase. Yet, a further aspect of the invention is a method for the purification of a nucleic acid, comprising the steps of (a) providing the nucleic acid in a sample, whereby the sample is dissolved in a liquid composition comprising a water-miscible liquid cyclic acetal, an aqueous buffer, and a chaotropic agent; followed by (b) providing the solid phase and contacting the liquid composition of step (a) with the solid phase, thereby adsorbing the nucleic acid onto the solid phase; followed by (c) separating the solid phase with the adsorbed nucleic acid from the liquid phase; (d) optionally washing with a washing solution the solid phase with the adsorbed nucleic acid; followed by (e) contacting the solid phase with the adsorbed nucleic acid with a desorption solution, thereby desorbing the nucleic acid from the solid phase and dissolving the nucleic acid in the solution; followed by (f) separating the solution with the nucleic acid from the solid phase, thereby purifying the nucleic acid; and optionally (g) precipitating the nucleic acid from the solution of step (f) and isolating the precipitated nucleic acid, thereby further purifying the nucleic acid. Yet, a further aspect of the invention is a composition comprising a liquid cyclic acetal and magnetic particles with a silica surface. Yet, a further aspect of the invention is a kit of parts, comprising packaging material, containers, and (a) a liquid cyclic acetal selected from the group consisting of 2-methyl-1,3-dioxolane, 2,2-dimethyl-1,3-dioxolane, 2-methoxy-1,3-dioxolane, DL-alpha, beta-isopropylideneglycerol, 1,3-dioxolane, 1,3-dioxane, 5-hydroxy-1,3-dioxane and 4-hydroxymethyl-1,3-dioxolane, 1,3-dithiolane and a mixture thereof, (b) a concentrated stock solution of a buffer salt and a chaotropic agent is selected from the group consisting of guanidine hydrochloride, guanidine thiocyanate, guanidine isothiocyanate, urea, sodium acetate, an alkali perchlorate, an alkali halogenide, and mixtures thereof; and (c) chromatographic and filtering material comprising a material with a surface capable of interacting with the phosphate residues in the backbone of nucleic acids. Yet, a further aspect of the invention is a kit of parts, comprising packaging material, containers, and (a) a suspension of silica-coated magnetic particles in a liquid cyclic acetal selected from the group consisting of 2-methyl-1,3-dioxolane, 2,2-dimethyl-1,3-dioxolane, 2-methoxy-1,3-dioxolane, DL-alpha, beta-isopropylideneglycerol, 1,3-dioxolane, 1,3-dioxane, 5-hydroxy-1,3-dioxane and 4-hydroxymethyl-1,3-dioxolane, 1,3-dithiolane and a mixture thereof; and (b) a concentrated stock solution of a buffer salt and a chaotropic agent is selected from the group consisting of guanidine hydrochloride, guanidine thiocyanate, guanidine isothiocyanate, urea, sodium acetate, an alkali perchlorate, and an alkali halogenide. Yet, a further aspect of the invention is a method for determining the presence of a nucleic acid in a sample, comprising the steps of: (a) forming a composition containing (i) the sample, (ii) an aqueous buffer, (iii) a chaotropic agent, (iv) a liquid cyclic acetal, whereby the sample is dissolved in the liquid composition; (b) contacting the composition of step (a) with a solid phase, thereby adsorbing the nucleic acid onto the solid phase; (c) separating the solid phase with the adsorbed nucleic acid from the liquid phase; (d) optionally washing with a washing solution the solid phase with the adsorbed nucleic acid; followed by (e) contacting the solid phase with the adsorbed nucleic acid with an aqueous desorption solution containing solutes in a lower concentration compared to the composition of step (a), thereby desorbing the nucleic acid from the solid phase and dissolving the nucleic acid in the solution; followed by (f) separating the solution with the nucleic acid from the solid phase, thereby purifying the nucleic acid; and (g) detecting in the solution of step (f) the presence of the nucleic acid, thereby determining the presence of the nucleic acid.

DETAILED DESCRIPTION OF THE INVENTION

The present invention provides new compositions and methods for the purification of nucleic acids. Certain terms are used with particular meaning, or are defined for the first time, in this description of the present invention. For the purposes of the present invention, the terms used are defined by their art-accepted definitions, when such exist, except that when those definitions conflict or partially conflict with the definitions set forth below. In the event of a conflict in definition, the meaning of a terms is first defined by any of the definitions set forth below.

The term "comprising" is used in the description of the invention and in the claims to mean "including, but not necessarily limited to".

The articles "a" and "an" are used herein to refer to one or to more than one (i.e., to at least one) of the grammatical object of the article. By way of example, "a compound" means one compound or more than one compound.

When designating a range of numerical values such as a concentration range, the range is indicated by the word "between", followed by a first value n1 and a second value n2. The lower boundary of the designated range is understood as being the value equal to or higher than the first value. The higher boundary of the designated range is understood as being the value equal to or lower than the second value". Thus, a value x the designated range is given by n1≦x≦n2.

Further, it is understood that the term "about" in combination with a numerical value n indicates a value x in the interval given by the numerical value±5% of the value, i.e., n−0.05*n≦x≦n+0.05*n. In case the term "about" in combination with a numerical value n describes a preferred embodiment of the invention, the value of n is most preferred, if not indicated otherwise.

An "acetal" is defined as geminal diether R(R1)C(OR2)(OR3), whereby R1=H and R, R2 or R3=aliphatic (aliphatic residue may also contain other atoms than C) or aromatic. Thus, an acetal is a molecule in which two single bonded oxygens are attached to the same carbon atom. Ketals, considered a subclass of acetals, are also geminal diethers (R1=C, aliphatic or aromatic). Ketals are understood as being encompassed by the term "acetal".

Formation of an acetal usually occurs when the hydroxyl group of a hemiacetal becomes protonated and is lost as water. The oxonium ion that is produced is then rapidly attacked by a molecule of alcohol. Loss of the proton from the attached alcohol results in the acetal.

Also encompassed by the invention and the term "acetal" are those compounds in which one or both of the oxygen atoms of the geminal diether are replaced by sulfur. Thioacetals are the sulphur analogue of acetals. They are prepared in a similar way to acetals: by reacting a thiol with an aldehyde. Dithioacetals, are prepared similarly to thioacetals, which are intermediates. Such reactions typically employ either a Lewis or Brønsted acid catalyst.

In a "cyclic acetal" (or ketal) the group R2 is covalently linked with R3 to form a cycle. The cyclic acetals or ketals are formed by reaction of diols (or thiols) with aldehydes or ketones, respectively. Since cyclic ketals are a subclass of cyclic acetals, the definition of cyclic acetals herein shall also include cyclic ketals, as well as the sulphur-containing analogues thereof. Importantly, cyclic acetals are distinguished from cyclic ethers. It is recalled that an acetal is a molecule in which two-single bonded oxygens are attached to the same carbon atom. This distinction can be explained with respect to cyclic isomers having the formula $C_4H_8O_2$ including 1,4-dioxane, 1,2-dioxane and 1,3-dioxane. 1,4-Dioxane, often just called dioxane, is classified as an ether, with each of its two oxygen atoms forming an ether functional group. 1,2-dioxane and 1,3-dioxane are isomeric compounds. The former is a peroxide, the latter a cyclic acetal. Compared to 1,3-dioxane, 1,4-dioxane is more stable against hydrolysis under acidic conditions. 1,3-dioxane is hydrolyzed to form formaldehyde and pentanediol while 1,4-dioxane is hydrolyzed to form ethylene glycol, consistent with the structure of the educt with the two ether group forming oxygens at two different C-atoms.

The term "water-miscible" indicates that at room temperature and normal atmospheric pressure a water-miscible compound can be dissolved in water at a ratio equal or greater than 1% (percent) volume by volume, to form a homogeneous aqueous liquid phase. An unlimited water-miscible compound, when mixed with water, forms a homogeneous liquid phase at any water/compound ratio. In case the solubility of the water-miscible compound is limited in water, the compound may form a separate phase in addition to the aqueous phase. The compound may also form an emulsion, especially in the presence of a surfactant.

A compound or a composition is a "liquid" if at room temperature and normal atmospheric pressure the compound is in the "liquid" state and forms a liquid phase.

The terms "aqueous", "aqueous" phase and "aqueous" solution describe a liquid phase of which the solvent portion comprises water. However, other solvents such as a water-miscible organic solvent can be present in the solvent portion, too. In view of the presence of other solvents a solution is considered "aqueous" when between 30% and 100%, measured as volume by volume [v/v], of the solvent portion is water.

A "chaotropic agent" is a compound which weakens hydrophobic interactions of the components in an aqueous solution. Certain ions in water will tend to increase hydrophobic interactions, while other ions will decrease hydrophobic interactions. Which ions have a tendency to which effect is described by what is called a Hofmeister series. The series is as follows:

Cations:

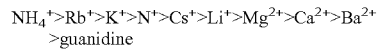

Anions:

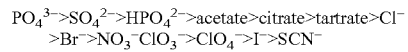

Ions on the left are said to be "kosmotropic" and increase the strength of hydrophobic interactions and thus will precipitate or "salt out" proteins at a high concentrations. Ions on the right are "chaotropic" and tend to weaken hydrophobic interactions. The Hofmeister series explains why a guanidine salt is a protein denaturant. It weakens hydrophobic interactions causing proteins to denature. In addition to the above, there are also chaotropic compounds which are non-ionic. An example therefor is urea.

In the present document it is understood that the term "a nucleic acid" denotes at least one nucleic acid. Furthermore, the term "a nucleic acid" also may indicate a mixture of nucleic acids. The term "nucleic acid" encompasses RNA, DNA, or both.

The term "solid phase" to which a nucleic acid is adsorbed is understood as being a substrate which is insoluble in the compositions according to the invention. A preferred solid phase is a substrate with a surface capable of interacting with the phosphate groups of the backbone of nucleic acids. The solid phase may be in the form of porous or non-porous particles, powdered particles, or fibers. A solid phase consisting of fleece material which comprises a plurality of non-woven fibers is also encompassed. Preferred solid phases consist of glass. Preferred solid phases are porous or non-porous mineral substrates such as silica, quartz, celites or other materials with oxidic surfaces (including, e.g., zirconium oxide, aluminum oxide, and other metal oxides) or mixtures thereof. Also, the term "solid phase" encompasses magnetically attractable particles coated with silica, glass, quartz, or celites. Further, it is understood that a substrate in the form of "powder" or "powdered" material refers to finely divided material which, when dispersed in a liquid composition according to the invention, produces a suspension. The term "powder" or "powdered" material is intended to include tablets, in which the powdered material has been aggregated, but still yields a suspension when combined with a liquid phase.

The term "silica" as used within this application denotes materials which are mainly build up of silicon and oxygen. These materials comprise silica, silicon dioxide, silica gel, fumed silica gel, diatomaceous earth, celite, talc, quartz, glass, glass particles including all different shapes of these materials. Glass particles, for example, may comprise particles of crystalline silica, soda-lime glasses, borosilicate glasses, and fibrous, non-woven glass.

The term "magnetic particle" denotes a particle with paramagnetic or superparamagnetic properties. That is to say, the particle is magnetically displaceable but does not retain any magnetisation in the absence of an externally applied magnetic field.

The term "sample" (or "sample material") as used herein refers to a complex sample, more preferred a biological sample. A complex sample may contain a plurality of organic and inorganic compounds which are desired to be separated from the nucleic acid. The term "sample" also encompasses an aqueous solution containing nucleic acids derived from other origins, e.g., from chemical or enzymatic reaction mixtures, or from a previous purification of biological sample material. The term biological sample, from which nucleic acids are purified, encompasses samples comprising viruses or bacterial cells, as well as isolated cells from multicellular organisms such as human and animal cells as well as tissues and cell cultures. Particularly, the sample can contain leucocytes, and other immunologically active cells, chemical compounds with a low and/or a high molecular weight such as haptens, antigens, antibodies and nucleic acids. The sample can be whole blood, blood serum, blood plasma, cerebral fluid, sputum, stool, biopsy specimens, bone marrow, oral rinses, tissues, urine or mixtures thereof. The present invention also encompasses biological samples such as a fluid from the human or animal body; preferably the biological sample is blood, blood plasma, blood serum or urine. The blood plasma is preferably EDTA, heparin or citrate blood plasma. In an embodiment of the invention the biological sample comprises bacterial cells, eukaryotic cells, viruses or mixtures thereof. A biological sample as exemplified above, preferably in a processed form such as a lysate, can be part of the composition from which the (target) nucleic acid is adsorbed to the substrate. Also encompassed by the term "biological sample" are cells from plants, and fungi as well as single cell organisms.

A preferred sample according to the invention is a lysate. A "lysate" or a "lysed sample" can be obtained from a complex sample and/or biological sample material comprising tissue, cells, bacteria or viruses, whereby the structural integrity of the material is disrupted. To release the contents of cells, tissue or, more generally, from the particles which make up a biological sample, the material may be treated with enzymes or with chemicals to dissolve, degrade or denature the cellular walls and cellular membranes of such organisms. This process is encompassed by the term "lysis". It is common to use chaotropic agents such as a guanidine salt and/or anionic, cationic, zwitterionic or non-ionic detergent when nucleic acids are set free in the lysis process. It is also an advantage to use proteases which rapidly degrade enzymes with nucleolytic activity and other unwanted proteins. In case there remains particulate, i.e., undissolved matter of the sample material following the lysis process, the particulate matter is usually separated from the lysate to result in a cleared lysate. This can be done, e.g., by way of filtering or centrifugation. In such a case the cleared lysate is processed further, e.g., by a method according to the invention. Thus, the term "lysed sample" encompasses a cleared lysate.

Nucleic acids which are set free can be purified by way of binding (adsorbing) to a solid phase, washing said solid phase with the bound nucleic acids and releasing, i.e., desorbing said nucleic acids from said mineral support.

According to the invention, the binding step is performed with a composition comprising a water-miscible liquid cyclic acetal, an aqueous buffer, and a chaotropic agent.

The invention also encompasses a composition comprising a water-miscible liquid cyclic acetal, an aqueous buffer, a chaotropic agent and a nucleic acid. Furthermore, the invention encompasses a composition comprising a water-miscible liquid cyclic acetal, an aqueous buffer, a chaotropic agent and a complex sample containing a nucleic acid. Moreover, the invention encompasses a composition comprising a water-miscible liquid cyclic acetal, an aqueous buffer, a chaotropic agent and a biological sample containing a nucleic acid.

Acetals as carbonyl derivatives are characterized by their stability and lack of reactivity in neutral to strongly basic environments. Preferably, the acetal is a non-glycosidic acetal. More preferred, the acetal is a cyclic acetal. Cyclic acetals offer stability against all types of nucleophiles and bases. Due to their cyclic nature cyclic acetals are more stable under acidic conditions than normal acetals. Cyclic acetals offer high stability at least down to pH 4 (Greene, T. W., Wuts, P. G. M., Protective Groups in Organic Synthesis, John Wiley & Sons, Inc., New York (1999) 308-322, 724-727). This feature makes cyclic acetals particularly suited as additives promoting the adsorption of a nucleic acid to a solid phase. A preferred cyclic acetal is selected from the group consisting of 2-methyl-1,3-dioxolane, 2,2-dimethyl-1,3-dioxolane, 2-methoxy-1,3-dioxolane, DL-alpha, beta-isopropylideneglycerol, 1,3-dioxolane, 1,3-dioxane, 5-hydroxy-1,3-dioxane and 4-hydroxymethyl-1,3-dioxolane, 1,3-dithiolane and a mixture thereof. 1,3-dioxolane is a colorless liquid that is miscible with water and most common organic solvents. 1,3-dioxolane is characterized by a low toxicity. A mixture of 5-hydroxy-1,3-dioxane and 4-hydroxymethyl-1,3-dioxolane is also known as "glycerol formal". Glycerol formal is a low odour and low toxic, slowly evaporating solvent. There is no solubility limit for glycerol formal in water. Glycerol formal is very stable under both acid and base conditions (minimal pH 2.8).

According to the invention, the preferred concentration of the acetal in the composition is between 1% and 60%, measured as "volume by volume", also referred to as [v/v]. Even more preferred, the concentration of the acetal is between 10% [v/v] and 40% [v/v]. Even more preferred, the concentration of the acetal is between 15% [v/v] and 30% [v/v].

The preferred pH value of the composition according to the invention is between 4 and 7.5. Even more preferred, the pH value is between 6.0 and 7.5. It is obvious for the artisan to produce suitable aqueous buffered solutions. In order to stabilize the pH value, a buffer is present in the composition according to the invention. Buffer systems which suitable for molecular biology purposes may be found, e.g., in Sambrook, Fritsch & Maniatis, Molecular Cloning, A Laboratory Manual, 3rd edition, CSHL Press, 2001. Preferred buffer substances are citric acid, phosphoric acid, N-(Carbamoylmethyl)-2-aminoethanesulfonic acid (ACES), N-(2-Acetamido)iminodiacetic acid (ADA), N,N-Bis(2-hydroxyethyl)-2-aminoethanesulfonic acid (BES), Tris-(hydroxymethyl)-aminomethane (TRIS), 2-Bis(2-hydroxyethyl)amino-2-(hydroxymethyl)-1,3-propanediol (BIS-TRIS), N-(2-Hydroxyethyl)piperazine-N'-(2-ethanesulfonic acid) (HEPES), 2-(N-Morpholino)ethanesulfonic acid (MES), 3-(N-Morpholino)propanesulfonic acid (MOPS), 3-(N-Morpholinyl)-2-hydroxypropanesulfonic acid (MOPSO), piperazine-N,N'-bis(2-ethanesulfonic acid) (PIPES), salts thereof, or other suitable substances.

In detail, the procedure for binding a nucleic acid (also referred to as target nucleic acid) to a solid phase such as, e.g., glass particles can be described as follows. It is preferably performed in the presence of a chaotropic agent with a concentration of between 0.5 M and 10 M, and preferably between 1 M and 5 M. Most preferred, the concentration of the chaotropic agent is between 2 M and 4 M. A preferred chaotropic agent is selected from the group consisting of guanidine hydrochloride, guanidine thiocyanate, guanidine isothiocyanate, urea, sodium acetate, an alkali perchlorate, an alkali iodide, lithium chloride, potassium chloride, and sodium chloride. Mixtures comprising one or more of the listed agents are also possible.

When lysing a biological sample in order to set free the nucleic acids or when binding the nucleic acid to the solid phase it is further preferred to use a detergent in the procedures, that is to say an anionic, cationic, zwitterionic or non-ionic detergent. Such detergents are well known to the person skilled in the art. Generally, a "detergent" is a surface active agent, also known as a surfactant. A detergent is capable of lowering the surface tension of the medium in which it is dissolved, and/or the interfacial tension with other phases, and, accordingly, is positively adsorbed at the liquid/vapor and/or at other interfaces. Thus, detergents are amphipathic molecules with polar (water soluble) and nonpolar (hydrophobic) domains. They are capable of binding to hydrophobic molecules or molecular domains to confer water solubility. Depending on its ionic characteristics, a detergent can be categorized as an ionic detergent, a non-ionic detergent, and a zwitterionic detergent. Ionic detergents can be further classified into either anionic detergents such as SDS (sodium dodecyl sulfate) LiDS (lithium dodecyl sulfate), sodium lauroyl sarcosine, 1-octanesulfonic acid, cholic acid, or deoxycholic acid, and cationic detergents such as cetyl trimethylammonium bromide (CTAB), trimethyl(tetradecyl)ammoniumbromide, lauryl trimethylammonium chloride (LTAB), lauryl trimethylammonium schloride (LTAC) or stearyl trimethylammonium chloride (STAC). Thus, these are usually highly protein denaturant. Non-ionic detergents such as Nonidet P40, TWEEN 20, TRITON X-100, BRIJ 35 P (ICI Americas Inc.), saponin, N,N-dimethyldodecylammine-N-oxide, N,N-dimethyldodecylamine-N oxide, or nonaethylene glycol monododecyl ether are usually less protein denaturant. This is also true for zwitterionic detergents such as 3-(N,N-dimethylpalmitylammonio) propanesulfonate, 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO) or Sulphobetaine 14. Zwitterionic compounds, also known as zwitterions, inner salts or dipolar ions are neutral compounds having formal unit electrical charges of opposite sign.

The composition according to the invention may thus also comprise a detergent. It is preferred that the composition comprises an anionic, cationic, zwitterionic or non-ionic detergent. It is even more preferred that the detergent in the composition is selected from the group consisting of Sodium dodecyl sulfate, Lithium dodecyl sulfate, Cetyltrimethylammoniumbromide, Deoxycholic acid, Sodium lauroyl sarcosine, TRITON-X100, TWEEN 20, Octyl beta-D-glucoside, Nonidet P40, BRIJ 35 P or Sulphobetaine 14. However, other detergents are possible.

Moreover, the composition may contain a protease. Generally, when using the combination of a chaotropic agent, a detergent and a protease for lysing a biological sample, the skilled artisan selects e chaotropic agent and the detergent and their concentrations in the composition according to the invention on the basis that proteolytic activity is preserved in the composition.

The composition according to the invention which additionally contains a nucleic acid is also referred to as an "adsorption solution" because the composition provides the conditions necessary for adsorbing the nucleic acid to a solid phase. Thus, another aspect of the invention is the use of a water-miscible liquid cyclic acetal for adsorbing a nucleic acid onto a solid phase. Yet, a further aspect of the invention is a method of using a water-miscible liquid cyclic acetal and a nucleic acid in a sample comprising the steps of (a) providing the nucleic acid in a sample, whereby the sample is dissolved in a liquid composition comprising a water-miscible liquid cyclic acetal, an aqueous buffer, and a chaotropic agent; followed by (b) providing the solid phase and contacting the liquid composition of step (a) with the solid phase, thereby adsorbing the nucleic acid onto the solid phase. Preferably, the sample has been treated in order to obtain a lysed sample.

To bring the sample in contact with the solid phase, i.e., the material with an affinity to nucleic acids, the sample is mixed with the material and incubated for a period of time sufficient for the binding to occur. Experts are usually familiar with the duration of the incubation step. This step can be optimized by determining the quantity of immobilized biological material on the surface at different points in time. Incubation times of between 1 second (s) and 30 minutes (min) can be appropriate for nucleic acids. After incubation, the solid phase with the adsorbed nucleic acid(s) is separated from the liquid. This may be achieved in general by gravity in the case a suspension of a pulverized solid phase such as glass powder is used. In the convenient case of nucleic acids bound to magnetic glass particles separation can be achieved by immobilizing the magnetic particles with a magnetic field and removing the liquid phase. For instance, the magnetic particles can be pulled to the wall of the vessel in which incubation was performed. The liquid containing the sample contents that are not bound to the magnetic particles can then be removed. The removal procedure used depends on the type of vessel in which incubation was performed. Suitable steps include removing the liquid via pipetting or aspiration. Another example is binding the nucleic acid in the adsorption solution to a glass fleece. Commercial kits often provide such a fleece at the bottom of a column. The adsorption solution containing the nucleic acid is transferred to the column and passed through the fleece by applying force. The term "force" includes gravitational force and, preferred, centrifugal force. Very much preferred is the "spin column" procedure wherein the adsorption solution is passed through the filter due to force being applied by way of centrifugation. Other ways to pass the adsorption solution through the fleece include the application of pressure or suction.

According to the invention, a preferred solid phase comprises a porous or non-porous silica substrate. More preferred, the solid phase comprises a substrate selected from the group consisting of glass fibers and quartz fibers. Also very much preferred, the solid phase comprises magnetic particles with a silica surface. Magnetizable particulate adsorbents are a very much preferred solid phase because they are suitable for automatic sample preparation. Ferrimagnetic and ferromagnetic as well as superparamagnetic particles are used for this purpose. Very much preferred magnetic glass particles are those described in WO 01/37291. It is very convenient to provide the magnetic particles as a suspension in the water-miscible liquid cyclic acetal according to the invention. Therefore, another aspect of the invention is a composition comprising a liquid cyclic acetal and magnetic particles with a silica surface. Preferably the particles are provided as powdered material. The magnetic glass particles used in the present invention may be provided in different formulations. It is possible to provide them in the form of a tablet, as a powder or as a suspension which is preferred. Preferably, these suspensions contain between 5 to 60 mg/ml magnetic glass particles. Also preferred, the silica-containing material is suspended in an aqueous buffered solution which may optionally contain a chaotropic agent in a concentration of between 1 M and 10 M, and preferably between 2 M and 6 M.

Yet, a further aspect of the invention is a method for the purification of a nucleic acid from a sample, comprising the steps of: (a) providing the nucleic acid in a sample, whereby the sample is dissolved in a liquid composition comprising a water-miscible liquid cyclic acetal, an aqueous buffer, and a chaotropic agent; followed by (b) providing the solid phase and contacting the liquid composition of step (a) with the solid phase, thereby adsorbing the nucleic acid onto the solid phase, thereby adsorbing the nucleic acid onto the solid phase; followed by (c) separating the solid phase with the adsorbed nucleic acid from the liquid phase; (d) optionally washing with a washing solution the solid phase with the adsorbed nucleic acid; followed by (e) contacting the solid phase with the adsorbed nucleic acid with a desorption solution, whereby the nucleic acid is desorbed from the solid phase, and dissolving the nucleic acid in the solution; followed by (f) separating the solution with the nucleic acid from the solid phase, thereby purifying the nucleic acid; and optionally (g) precipitating the nucleic acid from the solution of step (f) and isolating the precipitated nucleic acid, thereby further purifying the nucleic acid. The purification effect results from the behavior of DNA or RNA to bind to material with a glass surface under the conditions provided by the composition of the invention in the adsorption solution containing the nucleic acid to be purified.

Additionally, a detergent can also be used in the adsorption solution and provide advantage. The detergent aids in the process of releasing the nucleic acids. E.g., cells and tissues are lysed by detergents which disintegrate cellular membranes. In addition, detergents enhance the dissociation of nucleic acids from concomitant sample constituents such as protein. In addition, a detergent increases the binding of nucleic acids to solid phases, and when using a porous solid phase the detergent facilitates access of the liquid phase to the pore compartments of the solid phase.

The washing step may not always be necessary and therefore represents a non-mandatory option. Performing the washing step is opted for by the skilled person depending on the sample material from which the nucleic acid is to be purified. The purpose of the washing step(s) is to remove contaminants, i.e., undesired components of the sample material from the adsorbed nucleic acid. A washing solution is used that does not cause nucleic acid(s) to be released from the surface of the solid phase but that washes away the undesired contaminants as thoroughly as possible.

A washing step is preferably performed by incubating the material with the adsorbed nucleic acid(s) with the washing solution. The solid phase material is preferably resuspended during this step. Also preferred, in case the material is a glass fleece or a packing in a column, the washing step takes place by rinsing the column with the washing solution. Preferably, the washing solution is passed through the column by applying pressure, suction, centrifugal force or gravitational force. The contaminated washing solution is preferably removed just as in the step described above for binding the nucleic acid to the solid phase. After the last washing step, the material can be dried briefly in a vacuum, or the fluid can be allowed to evaporate. Prior to desorption, a pretreatment step using acetone may also be performed.

Preferably, the washing solution contains an organic solvent selected from the group consisting of a C1-C5 aliphatic alcohol, a liquid cyclic acetal, and tetraethylene glycol dimethyl ether (TDE); furthermore the washing solution preferably contains a chaotropic agent at a concentration between 0.5 M and 4 M. Preferably, the pH value of the washing solution is between pH 4 and pH 7.5, more preferred between pH 5 and pH 7, with pH 6 to pH 7 being most preferred. The preferred concentration of the organic solvent according to the invention in the washing solution is between 10% and 90% [v/v]. A very much preferred aliphatic alcohol is ethanol or isopropanol.

Under the conditions provided by the washing solution preferably greater than 40%, more preferred greater than 50%, more preferred greater than 70%, more preferred greater than 80%, even more preferred greater than 90%, even more preferred greater than 95%, even more preferred greater than 99% of the nucleic acids remain adsorbed to the solid phase.

In order to reverse the conditions for adsorption, the concentration of the chaotropic agent and/or the water-miscible liquid cyclic acetal is decreased resulting in desorption of the nucleic acid(s) bound to the solid material. Thus, the invention also encompasses the method comprising the step of releasing the adsorbed nucleic acid (=desorbing) from the solid phase. Preferably; the process of separating the substrate, e.g., the magnetic glass particles, from the rest of the sample is done by pelleting the immobilized biological material, e.g., by gravity force or by the use of a magnet in the case of magnetic glass particles and removal of the supernatant. Then the magnetic glass particles with the immobilized biological material are resuspended in an aqueous solution with no or only a low amount of chaotropic agent and/or liquid cyclic acetal. Alternatively, the suspension can be diluted with a solution with no or only a low amount of chaotropic agent and/or liquid cyclic acetal. Buffers of this nature are known from DE 37 24 442 and Jakobi, R., et al., Anal. Biochem. 175 (1988) 196-201. An elution buffer, i.e., a desorption solution, has a low salt content and preferably a pH greater than 7.5, a pH of about 8 being most preferred. Preferably the desorption solution contains solutes in a lower concentration compared to the adsorption solution. Particularly preferred, the solutes are one or more buffer salts with a content of less than 0.2 M of dissolved matter. Thus, the preferred concentration of solutes in the desorption solution is in between 0 M and 0.2 M. In addition, the preferred desorption solution does not contain a chaotropic agent or an organic solvent. Preferably, the elution buffer contains the substance TRIS for buffering purposes. Also very much preferred, the elution buffer is demineralized water. The solution containing the purified nucleic acid(s) can now be used for other reactions. Optionally, the nucleic acid(s) can be precipitated from the solution using, e.g., ethanol or isopropanol.

The precipitate can also be subjected to further washing steps. Methods of this kind are well known to the skilled artisan are described in detail in Sambrook, Fritsch & Maniatis, Molecular Cloning, A Laboratory Manual, 3rd edition, CSHL Press, 2001.

For the desorption step conditions are chosen by the skilled artisan, under which the nucleic acids are released from the mineral support. Preferably, greater than 40%, more preferred greater than 50%, more preferred greater than 70%, more preferred greater than 80%, even more preferred greater than 90%, even more preferred greater than 95%, even more preferred greater than 99% of the nucleic acids are released from the mineral support.

Purification of a nucleic acid by way of adsorbing the same to a substrate such as a mineral substrate in the presence of a composition according to the invention can also applied to other complex mixtures. Examples therefor are known to the person skilled in the art of molecular biology and include reaction mixtures following, e.g., in-vitro synthesis of nucleic acids such as PCR, restriction enzyme digestions, ligation reactions, etc. Another application for purification of a nucleic acid by way of adsorbing the same to a solid phase in the presence of a composition according to the invention is the removal of pyrogenic contaminants which may have copurified with the nucleic acid.

With great advantage, the method according to the present invention is suitable for the purification of nucleic acids, i.e., RNA or DNA, from complex mixtures with other biological substances containing them. Thereby also mixtures of different nucleic acids may be purified, even mixtures containing a nucleic acid of interest in low abundance. Thus, the present invention also encompasses the purification of mixtures of specific nucleic acids in which the target nucleic acid(s) may be a minor component in terms of concentration (or may be present in low abundance).

The procedure described can also be used to isolate native or modified nucleic acids. Native nucleic acids are understood to be nucleic acids, the structure of which was not irreversibly changed compared with the naturally-occurring nucleic acids. This does not mean that other components of the sample can not be modified, however. Modified nucleic acids include nucleic acids that do not occur in nature, e.g., nucleic acids that are modified by attaching to them groups that are reactive, detectable or capable of immobilization. An example of this are biotinylated nucleic acids.

The invention also contemplates kits. Such kits known to the art comprise plasticware useful in the sample preparation procedure. Examples therefor are microwell plates in the 96 or 384 well format or just ordinary reaction tubes manufactured, e.g., by Eppendorf, Hamburg, Germany. The kits of the invention also comprise some or all other reagents for carrying out the methods according to the invention. Therefore, a kit can additionally contain a solid phase, i.e., a material with an affinity to nucleic acids. Preferably the solid phase comprises a material with a silica surface. Very much preferred, the solid phase comprises glass or quartz fibers. Also very much preferred, the solid phase is a composition comprising magnetic glass particles, i.e., magnetically attractable particles coated with glass. Another preferred material with an affinity to nucleic acids is anion exchanger. The kit can further or additionally comprise a lysis buffer containing, e.g., a chaotropic agent, a detergent or mixtures thereof. These components of the kit according to the invention may be provided separately in tubes or storage containers. Depending on the nature of the components, these may be even provided in a single tube or storage container. The kit may further or additionally comprise a washing solution which is suitable for the washing step of the solid phase when DNA or RNA is bound thereto. This washing solution may contain a water-miscible liquid cyclic acetal according to the invention and/or a chaotropic agent in a buffered solution or solutions with an acidic pH without a an acetal according to the invention and/or a chaotropic agent as described above. Often the washing solution or other solutions are provided as stock solutions which have to be diluted before use. The kit may further or additionally comprise a desorption solution, i.e., an elution buffer, that is to say a solution for desorbing the nucleic acid from the solid phase. A preferred desorption solution can be a buffer (e.g., 10 mM Tris, 1 mM EDTA, pH 8.0) or pure water. Further, additional reagents or buffered solutions may be present which can be used for the purification process of a nucleic acid, i.e., DNA or RNA.

A further aspect of the invention is a kit of parts, comprising packaging material, containers, and (a) a liquid cyclic acetal selected from the group consisting of 2-methyl-1,3-dioxolane, 2,2-dimethyl-1,3-dioxolane, 2-methoxy-1,3-dioxolane, DL-alpha, beta-isopropylideneglycerol, 1,3-dioxolane, 1,3-dioxane, 5-hydroxy-1,3-dioxane and 4-hydroxymethyl-1,3-dioxolane, 1,3-dithiolane and a mixture thereof, (b) a concentrated stock solution of a buffer salt and a chaotropic agent is selected from the group consisting of guanidine hydrochloride, guanidine thiocyanate, guanidine isothiocyanate, urea, sodium acetate, an alkali perchlorate, an alkali halogenide, and mixtures thereof; and (c) chromatographic and filtering material comprising a material with a surface capable of interacting with the phosphate residues in the backbone of nucleic acids.

A preferred embodiment of the present invention is to use the methods or the kits of the present invention in automatable methods as, e.g., described in WO 99/16781. Automatable method means that the steps of the method are suitable to be carried out with an apparatus or machine capable of operating with little or no external control or influence by a human being. Automated method means that the steps of the automatable method are carried out with an apparatus or machine capable of operating with little or no external control or influence by a human being. Only the preparation steps for the method may have to be done by hand, e.g., the storage containers have to be filled up and put into place, the choice of the samples has to be done by a human being and further steps known to the expert in the field, e.g., the operation of the controlling computer. The apparatus or machine may, e.g., add automatically liquids, mix the samples or carry out incubation steps at specific temperatures. Typically, such a machine or apparatus is a robot controlled by a computer which carries out a program in which the single steps and commands are specified. Preferred automated methods are those which are carried out in a high-throughput format which means that the methods and the used machine or apparatus are optimized for a high-throughput of samples in a short time. In another embodiment of the invention the methods or the kits according to the present invention are used in a semi-automated process which means that some reaction steps may have to be done manually. In a preferred embodiment of the invention, a suspension containing magnetic glass particles according to the present invention is taken from a storage container and partial volumes are added to different reaction vessels. Reaction vessels may be reaction tubes made from plastics eventually in microwell plate format contain 96 or 384 or more wells where a reaction can be carried out. However, these vessels may be made from other material, e.g., from steel.

A further aspect of the invention is a kit of parts, comprising packaging material, containers, and (a) a suspension of silica-coated magnetic particles in a liquid cyclic acetal selected from the group consisting of 2-methyl-1,3-dioxolane, 2,2-dimethyl-1,3-dioxolane, 2-methoxy-1,3-dioxolane, DL-alpha, beta-isopropylideneglycerol, 1,3-dioxolane, 1,3-dioxane, 5-hydroxy-1,3-dioxane and 4-hydroxymethyl-1,3-dioxolane, 1,3-dithiolane and a mixture thereof; and (b) a concentrated stock solution of a buffer salt and a chaotropic agent is selected from the group consisting of guanidine hydrochloride, guanidine thiocyanate, guanidine isothiocyanate, urea, sodium acetate, an alkali perchlorate, and an alkali halogenide.

Some of the organic compounds contemplated by the invention might be capable of dissolving certain plastic materials. Thus, when determining the nature of suitable storage or reaction vessels, the skilled artisan will determine in a limited number of obvious experiments the material which is suited best for executing the methods of the invention or for producing kits according to the invention.

In preferred embodiments of the invention the kits according to the invention are used for the purification of nucleic acids in research, bioanalytics or diagnostics. In preferred embodiments according to the invention the kits according to the invention or the methods according to the invention are used in a high-throughput format, i.e., in an automated method which allows the analysis of a high number of different samples in a very short time.

The nucleic acids isolated using the methods according to the invention can be used further as necessary. For instance, they can be used as a substrate for various enzymatic reactions. The nucleic acids can be used for a large number of purposes including sequencing, radioactive or non-radioactive labelling, amplification of one or more of the sequences they contain, transcription, hybridization with labelled probe nucleic acids, translation or ligation.

Yet, a further aspect of the invention is a method for determining the presence of a nucleic acid in a sample, comprising the steps of: (a) optionally lysing the sample; (b) forming a composition containing (i) the sample or the lysed sample of step (a), (ii) an aqueous buffer, (iii) a chaotropic agent, (iv) a water-miscible cyclic acetal, whereby the sample is dissolved in the liquid composition; (c) contacting the composition of step (b) with a solid phase, thereby adsorbing the nucleic acid onto the solid phase; (d) separating the solid phase with the adsorbed nucleic acid from the liquid phase; (e) optionally washing with a washing solution the solid phase with the adsorbed nucleic acid; followed by (f) contacting the solid phase with the adsorbed nucleic acid with an aqueous desorption solution containing solutes in a lower concentration compared to the composition of step (b), thereby desorbing the nucleic acid from the solid phase and dissolving the nucleic acid in the solution; followed by (g) separating the solution with the nucleic acid from the solid phase, thereby purifying the nucleic acid; and (h) detecting in the solution of step (g) the presence of the nucleic acid, thereby determining the presence of the nucleic acid.

It is preferred that the sample is a biological sample. Preferably, the nucleic acid is determined by amplification of the nucleic acid by means of the polymerase chain reaction using specific primers, a specific detection probe, and an amplification mixture, whereby amplification is monitored in real time. Also preferred is to determine the nucleic acid by hybridizing the nucleic acid to a hybridization probe and detecting and/or quantifying the hybrid. The skilled artisan is aware of the fact that not only a nucleic acid can serve as a hybridization probe but also a nucleic acid comprising one or more nucleoside analogues can be used. In addition, nucleic acid analogues such as PNA are known to the art as being capable of forming detectable hybrids with nucleic acids. It is understood that the nucleic acid to be determined is DNA or RNA. Very much preferred is the above method, whereby the nucleic acid is RNA and step (h) comprises (i) reverse transcribing the RNA to form a cDNA, (ii) subsequently amplifying, by means of the polymerase chain reaction, the cDNA, (iii) detecting the presence of the cDNA, thereby determining the presence of the nucleic acid.

The following examples are provided to aid the understanding of the present invention, the true scope of which is set forth in the appended claims. It is understood that modifications can be made in the procedures set forth without departing from the spirit of the invention.

All Examples given below were performed as variations of the standard workflow of the HIGH PURE (Roche Diagnostics Operations, Inc.) PCR Template Preparation Kit, user manual version April 2005, Roche Diagnostics GmbH, Mannheim, Germany, Catalogue No. 11796828001. Unless indicated otherwise, all working steps of the workflow were performed as indicated in said user manual.

Example 1

Purification of Total Nucleic Acids from Cultured Cells (A)

The workflow for purification of the nucleic acids (NAs) includes the following steps: Lysis of the sample in order to make the nucleic acids accessible for the purification process. Adsorption of the NAs onto the solid phase, separating the solid phase from the liquid phase and washing the solid phase with the bound. NAs, and desorbing the NAs from the solid phase.

Each sample consists of either $1 \times 10^6$ K562 cells or 200 µl EDTA blood from which nucleic acids are purified. Several samples are processed in parallel using essentially the same protocol but with different additives in the composition of the respective adsorption solution.

Sedimented cells are resuspended in 200 µl PBS buffer. Afterwards 200 µl binding buffer (6 M guanidine HCl, 10 mM urea, 10 mM Tris HCl, 20% [v/v] TRITON X-100, pH 4.4) and 40 µl Proteinase K solution (20 µg/µl dissolved in bidestilled water) are added to the cell suspension or EDTA blood and mixed by vortexing. The mixture is incubated for 10 min at 70° C. to lyse the samples. Subsequently, a 100 µl volume of one of the additives listed in Table 1 is mixed with a lysate.

TABLE 1

| Additives tested |
| --- |
| Tetraethylene Glycol Dimethyl Ether (TDE) |
| Isopropanol |
| 2-Methyl-1,3-Dioxolane |
| 2,2-Dimethyl-1,3-Dioxolane |
| 2-Methoxy-1,3-Dioxolane |
| DL-Alpha, Beta-Isopropylideneglycerol |
| 1,3-Dithiolane |
| 1,3-Dioxolane |
| Glycerol Formal (mixture of 5-Hydroxy-1,3-Dioxane and 4-Hydroxymethyl-1,3-Dioxolane |

Each of the additives is tested, whereby the additive is added in pure form. Thus, the concentration of each additive in the adsorption solution is between about 18% [v/v] and about 18.5% [v/v] (taking into account that some of the tested additives may not be entirely free of water).

Each adsorption solution is applied to a HIGH PURE spin column and processed according to standard procedure (HIGH PURE PCR Template Preparation Kit, user manual version July 2006, Roche applied Science, Germany, Catalogue No. 11796828001). Handling of the columns as well as washing and elution is performed according to the package insert of the HIGH PURE PCR Template Preparation Kit, version July 2006 (Roche Applied Science, Germany, Cat. No 11796828001). A first and a second washing buffer are used consecutively in each isolation/purification process. To prepare the first washing buffer (inhibitor removal buffer) a volume of 20 ml ethanol is added to 33 ml washing buffer 1 (5 M guanidine HCl, 20 mM Tris HCl, pH 6.6 (25° C.) final concentration after addition of ethanol) to result in an ethanol concentration of about 39% [v/v], respectively. To prepare the second washing buffer a volume of 80 ml ethanol is added to washing buffer 2 (20 mM NaCl, 2 mM Tris HCl, pH 7.5 (25° C.) final concentrations after addition of ethanol), to result in an ethanol concentration of about 80% [v/v], respectively.

Tables 2a and 2b indicate typical results regarding the outcome of the experiments. As shown, acetals are well suited and provide a higher yield than isopropanol (state of the art).

TABLE 2a

Yield and purity of nucleic acids isolated from culture cells

|  | 260/280 ratio | yield [µg] |
| --- | --- | --- |
| TDE | 2.02 | 16.96 |
| Isopropanol | 2.03 | 15.76 |
| 2-Methyl-1,3-Dioxolane | 2.005 | 16.72 |
| 2,2-Dimethyl-1,3-Dioxolane | 1.995 | 16.89 |
| 2-Methoxy-1,3-Dioxolane | 1.995 | 16.89 |
| DL-Alpha, Beta-Isopropylideneglycerol | 1.995 | 15.94 |
| 1,3-Dithiolane | 1.94 | 9.59 |

TABLE 2b

Yield and purity of nucleic acids isolated from 200 µl EDTA blood

|  | 260/280 ratio | yield [ng] |
| --- | --- | --- |
| TDE | 1.88 | 3975.32 |
| Glycerol Formal | 1.84 | 3856.59 |
| 1,3-Dioxolane | 1.88 | 2988.81 |
| Isopropanol | 1.90 | 2561.75 |

In addition, acetals provide the advantage in that they are less flammable than isopropanol. In addition, many acetals show only minor toxicity.

Example 2

Purification of Nucleic Acids from Cultured Cells (B)

Each sample consists of $1 \times 10^6$ K562 cells from which nucleic acids are purified. Several samples are processed in parallel using essentially the same protocol but with different additives in the composition of the respective adsorption solution.

Nucleic acids are purified from $1 \times 10^6$ K562 cells. Sedimented cells are resuspended in 200 µl PBS buffer. Afterwards 200 µl binding buffer (6 M guanidine HCl, 100 mM IVIES, 18.5% [v/v] TRITON X-100, pH 5.7) is added and mixed. Subsequently, a 100 µl volume of one of the additives listed in Table 1 is mixed with a lysate.

Each sample is applied to a spin column (HIGH PURE spin column) and processed according to standard procedure (HIGH PURE PCR Template Preparation Kit, user manual version July 2006, Roche applied Science, Germany, Cat. No 11796828001). A first and a second washing buffer are used consecutively in each isolation/purification process. To prepare the first washing buffer (inhibitor removal buffer) 20 ml ethanol or one of the additives listed in Table 1 are added to 33 ml washing buffer 1 (5 M guanidine HCl, 20 mM Tris HCl, pH 6.6 (25° C.) final concentration after addition of the additives) to result each in a concentration of about 39% [v/v], respectively. To prepare the second washing buffer 80 ml ethanol or one of the additives listed in Table 1 are added to washing buffer 2 (20 mM NaCl, 2 mM Tris HCl, pH 7.5 (25° C.) final concentrations after addition of additives), to result each in a concentration of about 80% [v/v], respectively. Comparisons are made, whereby three washing steps are applied to each sample, either with ethanol-containing or with another additive-containing wash buffers. The first washing step is performed with the first washing buffer, followed by two washing steps with the second washing buffer. Subsequently, the nucleic acids are desorbed from the solid phase. Except for the details given above, all steps further steps of the workflow are performed according to the standard procedure provided by the manufacturer (see manual for the HIGH PURE PCR Template Preparation Kit, user manual version July 2006, Roche Applied Science, Germany, Cat. No 11796828001).

Example 3

Purification of Total Nucleic Acids from Blood Samples

Each sample consists of a volume of 200 µl of EDTA whole blood. The solid phase used is silica fleece present in HIGH PURE spin columns (Roche Applied Science, Germany). Compounds tested for binding enhancement to the silica fleece are selected from Table 1.

EDTA blood is pooled and aliquots are subjected to nucleic acid isolation according to the following protocol: 200 µl whole EDTA blood is mixed with 200 µl Binding Buffer (6 M guanidine HCl, 100 mM MES, 18.5% [v/v] TRITON X-100, pH 5.7) and 40 µl Proteinase K (22 µg/µl dissolved in bi-destilled water) solution. The mixture is incubated for 10 min at 70° C. to effect lysis. Afterwards, 100 µl of one of the additives listed in Table 1 is added to a lysed sample and mixed. The mixture is applied to a spin column (HIGH PURE spin column, Roche Applied Science, Germany) for further processing. Handling of the columns as well as washing and elution is performed according to the package insert of the HIGH PURE PCR Template Preparation Kit, version July 2006 (Roche Applied Science, Germany, Cat. No 11796828001).

Example 4

Automated Nucleic Acid Isolation/Purification Workflow

For the demonstration of an automated workflow a MagnaPure LC instrument (Roche Applied Science, Germany) is used for the evaluation. Total nucleic acids are purified from $10^6$ cultured K562 cells. For the procedure the MAGNA PURE LC (Roche Diagnostics Operations, Inc.) DNA Isolation Kit—Large Volume (Roche Applied Science, Germany, Cat No 03310515001) is used. The standard procedure according to the instructions by the supplier using magnetically attractable particles dissolved in isopropanol is compared to a procedure with a similar amount of magnetic particles, however dissolved in one of the additives listed in Table 1 is mixed with a lysate. Apart from this variation, the workflow is performed exactly according to the package insert of the MAGNA PURE LC DNA Isolation Kit—Large Volume (Roche Applied Science, Germany, Cat No 03310515001, Version May 2006).

Example 5

Evaporation of Additives from Liquid Compositions

The effect of evaporation of organic solvents as additives in liquid compositions for the isolation/purification of nucleic acids is investigated. Several compositions are tested, whereby the compositions include organic solvents with differences in vapor pressure indicating a different evaporation rate. Evaporation affects stability of a reagent as well as reproducibility of the process in which the reagent is used. This is especially true in the case of automated systems for nucleic acid purification.

The evaporation rate of buffers with different compositions is determined. A volume of 200 µl of water is mixed with 200 µl binding buffer, containing 6 M guanidine-HCl, 10 mM urea, 10 mM Tris HCl, 20% TRITON X-100 (v/v), pH4.4 (25° C.) and 100 µl of a substance listed below in Table 3. Incubation of the mixtures is carried out for 30 min at 30° C. in a standard 1.5 ml eppendorf tube, whereby the lid is left open. Evaporation is assessed by weighing each tube before and after incubation and tabulating weight loss.

TABLE 3

Evaporation of different substances after 30 min from 20% [v/v] solutions

| Substance | vapor pressure at 20° C. [in mm Hg] | weight loss [in µg] |
| --- | --- | --- |
| tetraethylene glycol dimethyl ether (TDE) | <0.01 | 3.3 |
| diethylene glycol diethyl ether | 0.5 | 3.3 |
| ethyllactat | 2 | 3.6 |
| hydroxyaceton | 5.6 | 4.7 |
| glycerolformal | n/a | 5.2 |
| diethylene glycole dimethyl ether | 3 | 6.0 |
| polyethylene glycol 1000 | n/a | 8.2 |
| propylene glycol monomethyl ether acetate | 3.7 | 8.3 |
| ethanol | 44.6 | 9.3 |
| isopropanol | 33 | 14.0 |
| ethylene glycol diethyl ether | 9.4 | 14.4 |
| 1,3-dioxolane | 70 | 21.1 |
| propylene glycol dimethyl ether | 40 | 21.5 |
| metyl ethyl ketone | 71 | 28.6 |
| acetone | 184 | 32.3 |
| tetrahydrofuran | 143 | 44.4 |

When analyzing the amounts of weight loss one has to appreciate that the evaporated matter may also comprise water, apart from the organic solvent tested. The highest loss is observed for the Tetrahydrofuran containing buffer. Approximately 44.4 µg are evaporated from the 500 µl volume after 30 minutes. However, from the glycerol formal containing buffer only approximately 5.2 Mg evaporated.

What is claimed is:

1. A composition comprising a water-miscible, liquid cyclic acetal, an aqueous buffer, and a chaotropic agent.

2. The composition of claim 1 wherein the acetal is selected from the group consisting of 2-methyl-1,3-dioxolane, 2,2-dimethyl-1,3-dioxolane, 2-methoxy-1,3-dioxolane, DL-alpha, beta-isopropylideneglycerol, 1,3-dioxolane, 1,3-dioxane, 5-hydroxy-1,3-dioxane, 4-hydroxymethyl-1,3-dioxolane, and 1,3-dithiolane.

3. The composition of claim 1 wherein the concentration of the acetal in the composition is between 1% and 60% by volume.

4. The composition of claim 1 wherein the pH of the composition is between 4 and 7.5.

5. The composition of claim 1 wherein the chaotropic agent is selected from the group consisting of guanidine hydrochloride, guanidine thiocyanate, guanidine isothiocyanate, urea, sodium acetate, an alkali perchlorate, and an alkali halogenide.

6. The composition of claim 1 wherein the concentration of the chaotropic agent is between 0.5 M and 10 M.

7. A method for adsorbing a nucleic acid onto a solid phase comprising the steps of:
   providing a sample comprising the nucleic acid,
   dissolving the sample in a liquid composition comprising a water-miscible liquid cyclic acetal, an aqueous buffer, and a chaotropic agent, and
   contacting the liquid composition containing the dissolved sample with a solid phase whereby the nucleic acid is adsorbed onto the solid phase.

8. The method of claim 7 wherein the solid phase comprises a porous or non-porous silica substrate.

9. The method of claim 7 wherein the solid phase comprises a substrate selected from the group consisting of glass fibers and quartz fibers.

10. The method of claim 7 wherein the solid phase comprises magnetic particles with a silica surface.

11. The method of claim 7, further comprising the steps of:
   separating the solid phase with the adsorbed nucleic acid from the liquid composition,
   contacting the solid phase with the adsorbed nucleic acid with a desorption solution, thereby desorbing the nucleic acid from the solid phase and dissolving the nucleic acid in the solution,
   separating the solution with the nucleic acid from the solid phase, thereby purifying the nucleic acid, and optionally,
   precipitating the nucleic acid from the solution and isolating the precipitated nucleic acid, thereby further purifying the nucleic acid.

12. A composition comprising a liquid cyclic acetal and magnetic particles with a silica surface.

13. A method for determining the presence of a nucleic acid in a sample comprising the steps of:
   forming a liquid composition comprising a sample comprising a nucleic acid, an aqueous buffer, a chaotropic agent, a water-miscible liquid cyclic acetal, whereby the sample is dissolved in the liquid composition,
   contacting the liquid composition containing the dissolved sample with a solid phase, whereby the nucleic acid is adsorbed onto the solid phase,
   separating the solid phase with the adsorbed nucleic acid from the liquid composition,
   contacting the solid phase with the adsorbed nucleic acid with an aqueous desorption solution containing solutes in a lower concentration than the liquid composition, thereby desorbing the nucleic acid from the solid phase and dissolving the nucleic acid in the desorption solution, separating the solution with the nucleic acid from the solid phase, thereby purifying the nucleic acid, and detecting in the solution the presence of the nucleic acid, thereby determining the presence of the nucleic acid.

14. The method of claim 13 wherein the nucleic acid is RNA or DNA.

15. The method of claim 14 wherein the nucleic acid is RNA and the detection step comprises reverse transcribing the RNA to form a cDNA, amplifying, by means of a polymerase chain reaction, the cDNA, and detecting the presence of the cDNA, thereby determining the presence of the nucleic acid.

16. A kit of parts, the kit comprising packaging material, containers, a liquid cyclic acetal selected from the group consisting of 2-methyl-1,3-dioxolane, 2,2-dimethyl-1,3-dioxolane, 2-methoxy-1,3-dioxolane, DL-alpha, beta-isopropylideneglycerol, 1,3-dioxolane, 1,3-dioxane, 5-hydroxy-1,3-dioxane, 4-hydroxymethyl-1,3-dioxolane, and 1,3-dithiolane, a concentrated stock solution of a buffer salt and a chaotropic agent selected from the group consisting of guanidine hydrochloride, guanidine thiocyanate, guanidine isothiocyanate, urea, sodium acetate, an alkali perchlorate, and an alkali halogenide, and chromatographic and filtering material comprising a material with a surface capable of interacting with the phosphate residues in the backbone of nucleic acids.

17. A kit of parts, the kit comprising packaging material, containers, a suspension of silica-coated magnetic particles in a liquid cyclic acetal selected from the group consisting of 2-methyl-1,3-dioxolane, 2,2-dimethyl-1,3-dioxolane, 2-methoxy-1,3-dioxolane, DL-alpha, beta-isopropylideneglycerol, 1,3-dioxolane, 1,3-dioxane, 5-hydroxy-1,3-dioxane, 4-hydroxymethyl-1,3-dioxolane, and 1,3-dithiolane, and a concentrated stock solution of a buffer salt and a chaotropic agent selected from the group consisting of guanidine hydrochloride, guanidine thiocyanate, guanidine isothiocyanate, urea, sodium acetate, an alkali perchlorate, and an alkali halogenide.

* * * * *